US012788768B2

(12) United States Patent
Langier et al.

(10) Patent No.: US 12,788,768 B2
(45) Date of Patent: Nov. 10, 2026

(54) COMPOSITION COMPRISING CANNABINOIDS, AND/OR TERPENS, AND METHODS OF USING SAME

(71) Applicant: M.H MEDICANE LTD., Kadima Zoran (IL)

(72) Inventors: Sheila Langier, Kfar Saba (IL); Neta Rimmerman, Kfar Saba (IL)

(73) Assignee: M.H MEDICANE LTD., Kadima Zoran (IL)

(*) Notice: Subject to any disclaimer, the term of this patent is extended or adjusted under 35 U.S.C. 154(b) by 603 days.

(21) Appl. No.: 18/024,831

(22) PCT Filed: Sep. 5, 2021

(86) PCT No.: PCT/IL2021/051091
§ 371 (c)(1),
(2) Date: Mar. 6, 2023

(87) PCT Pub. No.: WO2022/049581
PCT Pub. Date: Mar. 10, 2022

(65) Prior Publication Data

US 2023/0338397 A1 Oct. 26, 2023

Related U.S. Application Data

(60) Provisional application No. 63/075,163, filed on Sep. 6, 2020.

(51) Int. Cl.

| | |
|---|---|
| ***A61K 31/00*** | (2006.01) |
| ***A61K 31/015*** | (2006.01) |
| ***A61K 31/045*** | (2006.01) |
| ***A61K 31/573*** | (2006.01) |
| ***A61K 31/704*** | (2006.01) |
| ***A61K 36/185*** | (2006.01) |
| ***A61P 11/02*** | (2006.01) |

(52) U.S. Cl.
CPC .......... *A61K 31/658* (2023.05); *A61K 31/015* (2013.01); *A61K 31/045* (2013.01); *A61K 31/573* (2013.01); *A61K 31/704* (2013.01); *A61K 36/3482* (2024.05); *A61P 11/02* (2018.01)

(58) Field of Classification Search
None
See application file for complete search history.

(56) References Cited

U.S. PATENT DOCUMENTS

2003/0021752 A1* 1/2003 Whittle ................ A61K 9/0031 424/45
2010/0152238 A1 6/2010 Mechoulam et al.

FOREIGN PATENT DOCUMENTS

CN 1253806 A 5/2000
WO 2017191630 A1 11/2017
WO WO-2018233884 A1 * 12/2018 ............... A61K 9/08

OTHER PUBLICATIONS

Wheeler, John. Nasal polyps: Unassuming growths with a powerful effect. Retrieved from the Internet on Jul. 22, 2025, https://www.mayoclinichealthsystem.org/hometown-health/speaking-of-health/nasal-polyps-pack-a-punch (Year: 2025).*
Cleveland Clinic. Nasal Polyps. Retrieved from the Internet on Jul. 22, 2025, https://my.clevelandclinic.org/health/diseases/15250-nasal-polyps. (Year: 2025).*
Translation of WO2018233884. Published 2018. Retrieved from Espacenet on Jul. 22, 2025, https://worldwide.espacenet.com/patent/search/family/062843201/publication/WO2018233884A1?q=wo2018233884. (Year: 2018).*
Seiberling et al. Efficacy of Dexamethasone Versus Fluticasone Nasal Sprays in Postoperative Patients with Chronic Rhinosinusitis with Nasal Polyps. Sage Journals. Vol. 33, Issue 5, Sep. 2019. (Year: 2019).*
Translation of CN1253806. Published 2000. Retreived from Espacenet on Jul. 22, 2025, https://worldwide.espacenet.com/patent/search/family/005275806/publication/CN1253806A?q=cn1253806 (Year: 2000).*
PubChem. Eucalyptol. Retrieved from the Internet on Jul. 22, 2025, https://pubchem.ncbi.nlm.nih.gov/compound/2758#section=Depositor-Supplied-Synonyms&fullscreen=true (Year: 2025).*
Moia et al. Lycopene used as Anti-inflammatory Nanodrug for the Treatment of Rheumathoid Arthritis: Animal assay, Pharmacokinetics, ABC Transporter and Tissue Deposition. Colloids and Surfaces B: Biointerfaces. vol. 188, published Apr. 2020. (Year: 2020).*
ElSohly, Mahmoud, and Waseem Gul. “Constituents of *Cannabis sativa*.” Handbook of cannabis 3.1093 (2014): 187-188. (Year: 2014).*
Sugawara K, Zákány N, Hundt T, Emelianov V, Tsuruta D, Schäfer C, Kloepper JE, Bíró T, Paus R. Cannabinoid receptor 1 controls human mucosal-type mast cell degranulation and maturation in situ. J Allergy Clin Immunol. Jul. 2013;132(1):182-93. doi: 10.1016/j.jaci.2013.01.002. Epub Feb. 26, 2013. PMID: 23453134.
Levy, J., et al. Type-2 Cannabinoid Receptors Maintain Epithelial Barrier in Aspirin-Exacerbated Respiratory Disease Journal of Allergy and Clinical Immunology, vol. 145, Issue 2, AB148, Feb. 2020. DOI: 10.1016/j.jaci.2019.12.478.
Chaboya-Hembree, J. Can Sinusitis be Helped with Cannabinoids? (n.d.). medicalmarijuana.com., Avaialbe online: [http://web.archive.org/web/20170716173411/https:/www.medicalmarijuana.com/medical-marijuana-treatments-cannabis-uses/can-sinusitis-be-helped-with-cannabinoids/], Jul. 16, 2017.
Tóth KF, Ádám D, Bíró T, Oláh A. Cannabinoid Signaling in the Skin: Therapeutic Potential of the “C(ut)annabinoid” System. Molecules. Mar. 6, 2019;24(5):918. doi: 10.3390/molecules24050918. PMID: 30845666; PMCID: PMC6429381.

(Continued)

*Primary Examiner* — Lauren Wells
(74) *Attorney, Agent, or Firm* — The Roy Gross Law Firm, LLC; Roy D. Gross

(57) ABSTRACT

The present invention is directed to a pharmaceutical composition including at least one cannabinoid or combination thereof, and methods of using same, such as for preventing, reducing or inhibiting the growth of a nasal polyp in a subject in need thereof.

8 Claims, 9 Drawing Sheets

(56) References Cited

OTHER PUBLICATIONS

Alves P, Amaral C, Teixeira N, Correia-da-Silva G. *Cannabis sativa*: Much more beyond Δ9-tetrahydrocannabinol. Pharmacol Res. Jul. 2020;157:104822. doi: 10.1016/j.phrs.2020.104822. Epub Apr. 23, 2020. PMID: 32335286.

Newton JR, Ah-See KW. A review of nasal polyposis. Ther Clin Risk Manag. Apr. 2008;4(2):507-12. doi: 10.2147/tcrm.s2379. PMID: 18728843; PMCID: PMC2504067.

Hopkins C. Chronic Rhinosinusitis with Nasal Polyps. N Engl J Med. Jul. 4, 2019;381(1):55-63. doi: 10.1056/NEJMcp1800215. PMID: 31269366.

Baron EP. Medicinal Properties of Cannabinoids, Terpenes, and Flavonoids in *Cannabis*, and Benefits in Migraine, Headache, and Pain: An Update on Current Evidence and *Cannabis* Science. Headache. Jul. 2018;58(7):1139-1186. doi: 10.1111/head.13345. PMID: 30152161.

Burstein S. Cannabidiol (CBD) and its analogs: a review of their effects on inflammation. Bioorg Med Chem. Apr. 1, 2015;23(7):1377-85. doi: 10.1016/j.bmc.2015.01.059. Epub Feb. 7, 2015. PMID: 25703248.

PCT International Search Report for International Application No. PCT/IL2021/051091, mailed Nov. 9, 2021, 6pp.

PCT Written Opinion for International Application No. PCT/IL2021/051091, mailed Nov. 9, 2021, 8pp.

* cited by examiner

COMPOSITION COMPRISING CANNABINOIDS, AND/OR TERPENS, AND METHODS OF USING SAME

CROSS-REFERENCE TO RELATED APPLICATIONS

This application is a National Phase of PCT Patent Application No. PCT/IL2021/051091 having International filing date of Sep. 5, 2021, which claims the benefit of priority of U.S. Provisional Patent Application No. 63/075,163, titled "COMPOSITION COMPRISING CANNABINOIDS, AND/OR TERPENS, AND METHODS OF USING SAME", filed Sep. 6, 2020, the contents of which are incorporated herein by reference in their entirety.

FIELD OF INVENTION

The present invention relates to cannabinoid compounds, pharmaceutical compositions comprising same, and method of use thereof, such as for treating a chronic inflammatory disease.

BACKGROUND

Chronic rhinosinusitis with nasal polyps (CRSwNP) is a chronic inflammatory disease of the sinonasal tissues. It is characterized by inflammatory tissue growth in nasal and paranasal cavity, which leads to nasal obstruction, secretion, loss of the sense of smell, anosmia, headaches, facial pain and reduced general well-being. Nasal polyps (NP) are believed to be a multifactorial disease usually associated with asthma and occasionally associated with aspirin sensitivity. It is usually a type 2 inflammatory disease with increased interleukin (IL) -5, -4 and -13, eosinophil infiltrate and local immunoglobulin (Ig) E production. NP treatments usually include corticosteroids and/or surgery, in which recurrence is very common.

The *Cannabis* plant (*Cannabis sativa*) has been in use for medical purposes for thousands of years. Medical *Cannabis* is nowadays prescribed for prevention of nausea and vomiting associated with cancer chemotherapy, and for the treatment of anorexia associated with AIDS and cancer.

*Cannabis* plants produce a group of natural chemicals called Cannabinoids, among them Δ9-tetrahydrocannabinol (THC), and Cannabidiol (CBD).

The immune-modulatory and anti-inflammatory properties of cannabinoids, for example CBD, have been shown in animal models of various inflammatory diseases including multiple sclerosis, diabetes mellitus, inflammatory bowel, and rheumatoid arthritis, inhibiting pro-inflammatory cytokine release including INFγ, TNFα, IL-1β, IL-6, IL-17 and Th2 cytokine release including IL-4, IL-5, IL-10, IL-13.

The use of a cannabinoid, e.g., CBD, for treating inflammatory diseases such as rheumatoid arthritis, multiple sclerosis and Crohn's Disease, and medicinal preparations containing CBD for use in treating such diseases, has been described.

Pharmaceutical compositions comprising cannabinoids, e.g., cannabidiol derivatives, which have analgesic, anti-anxiety, anticonvulsive, neuroprotective, antipsychotic, and anticancer, have been described.

Although it has been suggested to use cannabinoids, e.g., CBD, THC, etc., for treating various types of disease, e.g., inflammatory diseases, the state of the art does not describe or suggest the use of a specific cannabinoid, a terpene, or combinations or mixtures thereof, for prevention, reduction, or inhibition of the growth of a nasal polyp.

SUMMARY

The present invention provides a composition comprising: (a) at least one cannabinoid; (b) at least one terpene; or a combination of (a) and (b), and methods of using same, such as for reducing or inhibiting the growth of nasal polyps in a subject in need thereof, such as a subject afflicted with a chronic inflammatory disease, e.g., chronic rhinosinusitis.

According to a first aspect, there is provided a method for preventing or inhibiting the growth of a nasal polyp or reducing: the volume, the mass, the number of cells, or any combination thereof in a nasal polyp in a subject in need thereof, comprising administering to the subject a therapeutically effective amount of a pharmaceutical composition comprising at least one cannabinoid, thereby preventing or inhibiting the growth of the nasal polyp or reducing: the volume, the mass, the number of cells, or any combination thereof in a nasal polyp in the subject.

According to another aspect, there is provided a pharmaceutical composition comprising at least one cannabinoid and a pharmaceutically acceptable carrier, for use in the prevention or inhibition of the growth of a nasal polyp or reduction of: the volume, the mass, the number of cells, or any combination thereof in a nasal polyp in a subject in need thereof.

According to another aspect, there is provided kit comprising: (a) at least one cannabinoid selected from the group consisting of: CBD, CBG, THC, CBDV, and any combination thereof and (b) at least one glucocorticoid.

In some embodiments, the at least one cannabinoid is selected from the group consisting of: cannabidiol (CBD), cannabigerol (CBG), tetrahydrocannabinol (THC), and cannabidivarin (CBDV), and any combination thereof.

In some embodiments, the method further comprises a step of co-administering to the subject a therapeutically effective amount of a glucocorticoid.

In some embodiments, the glucocorticoid is dexamethasone or functional analog thereof.

In some embodiments, the glucocorticoid and the pharmaceutical compositions are co-administered sequentially or concomitantly.

In some embodiments, the subject is afflicted with chronic rhinosinusitis.

In some embodiments, the chronic rhinosinusitis comprises chronic rhinosinusitis with nasal polyps.

In some embodiments, the pharmaceutical composition further comprises least one terpene being selected from the group consisting of: Incensole acetate, Fenchol, Linalool, Humulene, Guaiol, Pinene, Carvacrol, Eucalyptol, 6-gingerol, Glycyrrhizin acid, Geraniol, Limonene, Lycopene, Terpineol, and any combination thereof.

In some embodiments, the administering is orally administering, nasally administering, or both.

In some embodiments, the administering is contacting the nasal polyp with the pharmaceutical composition.

In some embodiments, the at least one cannabinoid is selected from the group consisting of: CBD, CBG, THC, CBDV, and any combination thereof.

In some embodiments, the pharmaceutical composition comprises at least two cannabinoids being selected from the group consisting of: CBD, CBG, THC, and CBDV.

In some embodiments, the at least two cannabinoids are present in the pharmaceutical composition in a weight per weight ratio (w/w) ranging from 50:1 (w/w) to 1:50 (w/w).

In some embodiments, the at least two cannabinoids are present in the pharmaceutical composition in a weight per weight ratio (w/w) ranging from 25:1 (w/w) to 1:10 (w/w).

In some embodiments, the at least one cannabinoid is present in the pharmaceutical composition in an amount ranging from 0.1 ng to 500 mg.

In some embodiments, the kit further comprises instructions for administering the at least one cannabinoid and the at least one glucocorticoid in a mole per mole (m/m) ratio ranging from 15:1 (m/m) to 1:1 (m/m), to a subject in need thereof.

In some embodiments, the administering is sequentially administering or concomitantly administering.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Method of treatment

Figure 1A:
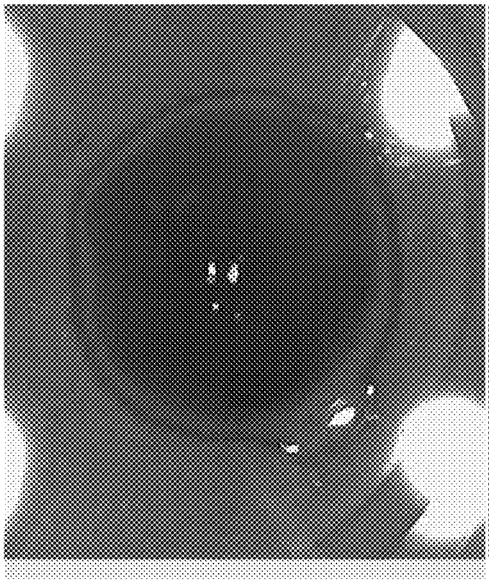
FIGS. 1A-1D include micrographs showing that nasal polyp cells/tissue pieces are starting to detach and disaggregate from the main polyp (arrows) after 3 h of cannabidiol (CBD; 150 μM) incubation. (1A) Time 0, vehicle; (1B) 3 hours of incubation, vehicle; (1C) Time 0, CBD; and (1D) 3 hours of incubation, CBD.
Figure 1B:
Figure 1C:
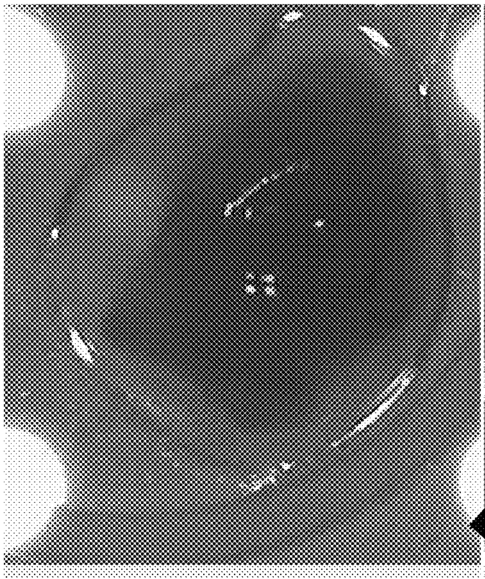
Figure 1D:
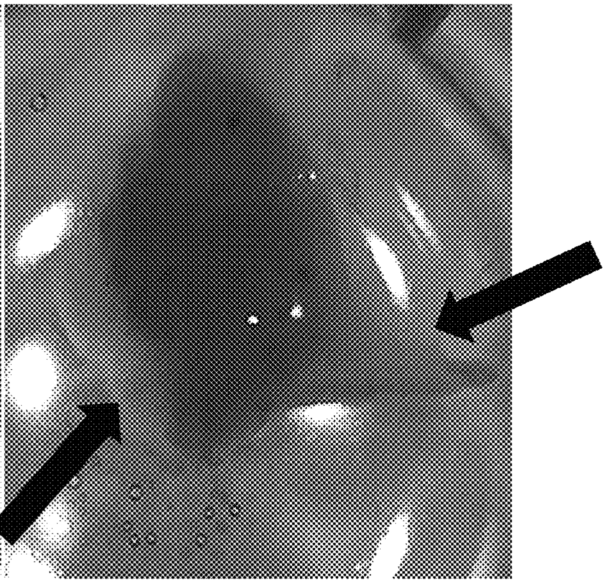

According to some embodiments, there is provided a method for preventing or inhibiting the growth of a nasal polyp or reducing: the volume, the mass, the number of cells, or any combination thereof in a nasal polyp in a subject in need thereof, comprising administering to the subject a therapeutically effective amount of a pharmaceutical composition comprising at least one cannabinoid, thereby preventing or inhibiting the growth of the nasal polyp or reducing: the volume, the mass, the number of cells, or any combination thereof in a nasal polyp in the subject.

As used herein, the term "nasal polyps" encompasses any noncancerous growth within the nasal cavity and/or sinus.

In some embodiments, the method comprises decolorizing a nasal polyp contacted with the composition of the invention.

In some embodiments, a nasal polyp contacted with the composition disclosed herein, is decolorized.

In some embodiments, a subject treated according to the method disclosed herein, is characterized by or comprises at least one decolorized nasal polyp.

In some embodiments, at least 5%, at least 15%, at least 30%, or at least 50% of the nasal polyps in a subject treated according to the method of the invention are decolorized, or any value and range therebetween. Each possibility represents a separate embodiment of the invention.

In some embodiments, decolorized is compared to a control.

In some embodiments, a control comprises a nasal polyp uncontacted with the composition of the invention.

In some embodiments, a control comprises a nasal polyp refractory to the method of the invention.

In some embodiments, a subject is afflicted with nasal polyps, per se, e.g., meaning the subject is not afflicted with another disorder or a disease related to nasal polyps. In some embodiments, "related to" refers to the nasal polyps being the causing agent inducing the development of a disorder or a disease or being the result of a disorder or a disease.

In some embodiments, the subject is afflicted only with nasal polyps.

In some embodiments, the subject is afflicted with nasal polyps and a background disorder or a disease.

In some embodiments, the subject is at risk of developing nasal polyps.

In some embodiments, the subject is afflicted with chronic rhinosinusitis.

In some embodiments, chronic rhinosinusitis comprises chronic rhinosinusitis with nasal polyps.

In some embodiments, "at risk" refers to increased likelihood of the subject to develop nasal polyps compared to a control.

In some embodiments, a control comprises a healthy subject.

In some embodiments, a control comprises a subject not afflicted with an inflammatory disease. In some embodiments, a control comprises a subject not afflicted with asthma.

In some embodiments, increased comprises at least: 5%, 15%, 25%, 50%, 75%, 100%, 150%, 250%, 500%, or 1,000% increase, or any value and range therebetween. Each possibility represents a separate embodiment of the invention. In some embodiments, increased comprises 1-20%, 15-65%, 20-120%, 75-250%, 150-500%, 350-850%, or 100 1,000%. Each possibility represents a separate embodiment of the invention.

In some embodiments, reducing or inhibiting the growth of nasal polyps comprises reducing: the volume of nasal polyps, the number of cells in nasal polyps, the volume of extracellular fluid accumulated in the nasal polyps, the rate of extracellular fluid accumulation in the nasal polyps, the rate of metaplastic alteration of epithelial cells covering the nasal polyps (e.g., from respiratory epithelium to squamous epithelium), the number of squamous epithelial cells covering the nasal polyps, the area of squamous epithelium covering the nasal polyps, the ratio between the area covered by squamous epithelium to the area covered by respiratory epithelium of the nasal polyps, or any combination thereof.

In some embodiments, the method comprises reducing the volume of nasal polyps. In some embodiments, the method comprises reducing the number of cells of nasal polyps. In some embodiments, the method comprises reducing or inhibiting inflammation of nasal polyps. In some embodiments, the method comprises reducing or inhibiting migration of an immune cell towards or to nasal polyps. In some embodiments, the method comprises reducing Th2-biased eosinophilic inflammatory response. In some embodiments, the method comprises reducing Th2-biased accumulation of any immune cells involved in the inflammatory response. In some embodiments, the method comprises reducing or inhibiting sinonasal microbial colonization or virus infection. In some embodiments, the method comprises reducing or inhibiting accumulation of extracellular fluid by the nasal mucosa. In some embodiments, the method comprises reducing or inhibiting necrosis or cell death of cells of the nasal mucosa. In some embodiments, the method comprises reducing or inhibiting secretion of molecules from the nasal mucosa, wherein such molecules trigger or induce Th2 inflammatory response, immune cell recruitment, or both.

As used herein, the term "Th2 inflammatory response" refers to a response of the immune system of an organism, which includes interleukins (IL), including but not limited to IL-4, -5, and -13, which relate to the promotion of immunoglobulin E (IgE) and eosinophilic responses in atopy, and an inflammatory response.

As used herein, the terms "Th2 inflammatory response" and "type 2 inflammatory response" are interchangeable.

In some embodiments, the at least one cannabinoid comprises or consists of a phytocannabinoid.

In some embodiments, the at least one cannabinoid comprises or consists of an endocannabinoid, a metabolite thereof, an endocannabinoid-like molecule, or any combination thereof.

As used herein, the term "endocannabinoid-like molecule" refers to any compound that is structurally related to a true endocannabinoid. In some embodiments, the endocannabinoid-like molecule is devoid of highly unsaturated fatty acids. In some embodiments, the endocannabinoid-like molecule does not bind to a cannabinoid receptor. In some embodiments, the endocannabinoid-like molecule binds to a cannabinoid receptor with lower binding affinity compared to an endocannabinoid or a metabolite thereof. In one embodiment, an endocannabinoid-like compound is selected from a group comprising N-acylethanolamines, or N-acylglycines. In one embodiment, an endocannabinoid-like compound is selected from a group comprising 2-monoacylglycerols.

Non-limiting examples of N-acylethanolamines include, but are not limited to: Anandamide, N-Palmitoylethanolamine, N-Oleoylethanolamine, N-Stearoylethanolamine, N-Docosahexaenoylethanolamine, N-Docosatetraenoylethanolamine, and N-homo-gamma-linolenoylethanolamine.

As used herein, the term "2-monoacylglycerols" encompasses any compound comprising a molecule of glycerol linked to a fatty acid by an ester bond, wherein the fatty acid is attached to a secondary alcohol of the glycerol molecule.

As used herein, a "phytocannabinoid" is a cannabinoid that originates in nature from the *Cannabis* plant. Examples of cannabinoids include, but are not limited to, cannabidiol (CBD), cannabidivarin (CBDV), (−)-$\Delta^9$-trans-tetrahydrocannabinol ($\Delta^9$-THC), (−)-$\Delta^9$-trans-tetrahydrocannabinolic acid ($\Delta^9$-THCA), (−)-$\Delta^9$-trans-tetrahydrocannabivarin ($\Delta^9$-THCV), (−)-$\Delta^9$-trans-tetrahydrocannabivarinic acid ($\Delta^9$-THCVA), cannabinol (CBN), cannabivarin (CBNV), cannabicyclol (CBL), cannabigerol (CBG), cannabigerovarin (CBGV), cannabidiolic acid (CBDA), cannabichromene (CBC), cannabichromenic acid (CBCA) and any derivative thereof.

In some embodiments, the present invention is directed to a composition derived from a plant extract. In some embodiments, a plant extract of the invention is derived from a plant comprising cannabinoids. In some embodiments, the plant extract of the invention is derived from a *Cannabis* plant. In some embodiments, the plant extract is derived from a specific species of the *Cannabis* genus.

According to some embodiments, the invention relates to a composition comprising at least one cannabinoid.

In some embodiments, the at least one cannabinoid is selected from: Cannabidiol (CBD), Tetrahydrocannabinol (THC), Cannabigerol (CBG), Cannabidivarin (CBDV), Cannabichromene (CBC), or any combination thereof.

In some embodiments, THC comprises or is Delta 9-THC ($\Delta$9-THC).

In some embodiments, the at least one cannabinoid is CBD. In some embodiments, the at least one cannabinoid is CBG.

In some embodiments, the composition comprises a single cannabinoid.

In some embodiments, the single cannabinoid is CBD.

In some embodiments, the single cannabinoid is CBG.

According to some embodiments, the invention relates to a composition comprising a plurality of cannabinoids.

In some embodiments, the composition comprises at least two cannabinoids being selected from: CBD, CBG, THC, and CBDV.

In some embodiments, the composition comprises CBD and CBG. In some embodiments, the composition comprises CBD and THC. In some embodiments, the composition comprises CBD and CBDV. In some embodiments, the composition comprises CBD, CBG, and THC. In some embodiments, the composition comprises CBD, CBG, and CBDV. In some embodiments, the composition comprises CBD, THC, and CBDV. In some embodiments, the composition comprises CBD, CBG, THC, and CBDV.

In some embodiments, the composition comprises CBG and THC. In some embodiments, the composition comprises CBG and CBDV. In some embodiments, the composition comprises CBG, THC, and CBDV.

In some embodiments, the composition comprises CBD and CBG is a weight per weight (w/w) or mole per mole ratio (m/m) ranging from: 25:1 to 1:25, 20:1 to 1:20, 15:1 to 1:15, 10:1 to 1:10, 5:1 to 1:5, 3:1 to 1:3, or is 1:1. Each possibility represents a separate embodiment of the invention.

In some embodiments, the composition comprises CBD and THC is a weight per weight (w/w) or mole per mole ratio (m/m) ranging from: 50:1 to 1:50, 40:1 to 10:1, 30:1 to 20:5, 25:1 to 5:1, 20:1 to 10:1, or 17:1 to 12:1. Each possibility represents a separate embodiment of the invention.

In some embodiments, the composition comprises CBG and THC is a weight per weight (w/w) or mole per mole ratio (m/m) ranging from: 50:1 to 1:50, 40:1 to 10:1, 30:1 to 20:5, 25:1 to 5:1, 20:1 to 10:1, or 17:1 to 12:1. Each possibility represents a separate embodiment of the invention.

In some embodiments, the composition comprises CBD and CBDV is a weight per weight (w/w) or mole per mole ratio (m/m) ranging from: 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, or is 1:1. Each possibility represents a separate embodiment of the invention.

In some embodiments, the composition comprises a combination of "high or medium CBD" and "low THC".

In some embodiments, the composition comprises a combination of "high or medium CBG" and "low THC".

In some embodiments, the composition comprises a combination of "high or medium CBG" and "low glucocorticoid".

In some embodiments, the composition comprises a combination of "high or medium CBD" and "low glucocorticoid" combination.

In some embodiments, "high", "medium", and "low", refer to a dose, concentration, weight, of a compound as described herein, being administered to a subject in need thereof, as disclosed herein.

As used herein, the term "high" and "low" refers to any case wherein the w/w or m/m ratio ranges as disclosed herein.

In some embodiments, "high" or "medium" is to be meant as being in the composition in a w/w or m/m ratio compared to "low" of at least: 100:1, 90:1, 80:1, 70:1, 60:1, 50:1, 40:1, 30:1, 20:1, 10:1, 8:1, 6:1, 4:1, 3:1, or 2:1, or any value and range therebetween.

In some embodiments, "high" or "medium" (e.g., CBD, or CBG) is to be meant to being in the composition in a weight or mole of at least 100-fold greater, at least 90-fold greater, at least 80-fold greater, at least 60-fold greater, at least 50-fold greater, at least 40-fold greater, at least 30-fold greater, at least 20-fold greater, at least 10-fold greater, at least-fold greater, at least 8-fold greater, at least 6-fold greater, at least 4-fold greater, or at least 2-fold greater, than the weight or mole of "low" (e.g., THC) in the composition. Each possibility represents a separate embodiment of the invention.

In some embodiments, the method comprises administering a first pharmaceutical composition comprising "high or medium CBD" and administering a second composition comprising a "low" glucocorticoid, e.g., sequentially administering, as disclosed herein.

In some embodiments, the method comprises administering a first pharmaceutical composition comprising "high or medium CBG" and administering a second composition comprising a "low" glucocorticoid, sequentially administering, as disclosed herein.

In some embodiments, the method comprises administering a first pharmaceutical composition comprising a "low" glucocorticoid and administering a second composition comprising, "high or medium CBD" e.g., sequentially administering, as disclosed herein.

In some embodiments, the method comprises administering a first pharmaceutical composition comprising a "low" glucocorticoid and administering a second composition comprising "high or medium CBG", e.g., sequentially administering, as disclosed herein.

In some embodiments, the composition further comprises at least one terpene being selected from: Incensole acetate, Fenchol, Linalool, Humulene, Guaiol, Pinene, Carvacrol, Eucalyptol, 6-gingerol, Glycyrrhizin acid, Geraniol, Limonene, Lycopene, Terpineol, or any combination thereof.

In some embodiments, the at least one cannabinoid, the at least one terpene, or both, are present in the pharmaceutical composition and administered at a dose of at least: 0.1 ng/kg/day, 1 ng/kg/day, 10 ng/kg/day, 100 ng/kg/day, 1 mg/kg/day, 5 mg/kg/day, 10 mg/kg/day, or 20 mg/kg/day, or any value and range therebetween. Each possibility represents a separate embodiment of the invention. In some embodiments, the at least one cannabinoid, the at least one terpene, or both, are present in the pharmaceutical composition and administered at a dose ranging from: 0.1-100 ng/kg/day, 1-1,000 ng/kg/day, 100-1,000 ng/kg/day, 100 ng/kg/day, 10 mg/kg/day, or 1-20 mg/kg/day. Each possibility represents a separate embodiment of the invention.

As used herein, the terms "administering", "administration", and like terms refer to any method which, in sound medical practice, delivers a composition containing an active agent to a subject in such a manner as to provide a therapeutic effect. One aspect of the present subject matter provides for dermal or transdermal administration of a therapeutically effective amount of a composition of the present subject matter to a patient in need thereof. Other suitable routes of administration can include oral, nasal, sublingual, buccal, or dermal. In some embodiments, administering is orally administering. In some embodiments, administering is nasally administering. In some embodiments, administering is orally administering and nasally administering. In some embodiments, administering is sublingual administering. In some embodiments, administering is sublingual administering and nasally administering. In some embodiments, administering is to the site of inflammation. In some embodiments, administering is to the site of an enlarged polyp. In some embodiments, administering is to the site of a polyp targeted for growth reduction and/or inhibition.

In some embodiments, administering comprises contacting a nasal polyp with the herein disclosed composition.

Administering the composition to a specific site in the subject may be performed with any method known in the art. This may include an inhalator.

In some embodiments, the method further comprising a step of co-administering to the subject a therapeutically effective amount of a glucocorticoid.

Types of glucocorticoids suitable for human therapy are common and would be apparent to one of ordinary skill in the art.

In some embodiments, the glucocorticoid is or comprises dexamethasone or functional analog thereof.

As used herein, the term "functional analog" refers to any derivative of dexamethasone as long as it maintains at least 70%, 80%, 90%, 95%, 99%, or 100% the activity of dexamethasone in reducing: the volume of nasal polyps, the number of cells in nasal polyps, the volume of extracellular fluid accumulated in the nasal polyps, the rate of extracellular fluid accumulation in the nasal polyps, the rate of metaplastic alteration of epithelial cells covering the nasal polyps (e.g., from respiratory epithelium to squamous epithelium), the number of squamous epithelial cells covering the nasal polyps, the area of squamous epithelium covering the nasal polyps, the ratio between the area covered by squamous epithelium to the area covered by respiratory epithelium of the nasal polyps, or any combination thereof, as disclosed herein, or any value at range therebetween. Each possibility represents a separate embodiment of the invention.

In some embodiments, the glucocorticoid and the pharmaceutical compositions are co-administered sequentially or concomitantly.

In some embodiments, the method comprises a first administering of the pharmaceutical composition comprising the at least one cannabinoid to the subject, and a second administering of the glucocorticoid to the subject. In some embodiments, the second administering comprises administering the glucocorticoid and the pharmaceutical composition of the invention.

In some embodiments, the method comprises a first administering of the glucocorticoid to the subject, and a second administering of a pharmaceutical composition comprising at least one cannabinoid the to the subject. In some embodiments, the first administering comprises administering the glucocorticoid and the pharmaceutical composition of the invention.

As a clarifying non-limiting example, a pharmaceutical composition comprising a first dose of at least one cannabinoid, e.g., CBD and/or CBG, is administered to the subject, and at a later period the glucocorticoid, e.g., dexamethasone, either solely or in conjunction with a second dose of the pharmaceutical composition as described above, is administered to the subject.

As yet another clarifying non-limiting example, a glucocorticoid, e.g., dexamethasone, either solely or in conjunction with a first dose of the pharmaceutical composition as described above is administered to the subject, and at a later period a pharmaceutical composition comprising a first or a second dose of at least one cannabinoid, e.g., CBD and/or CBG, is administered to the subject.

In some embodiments, the co-administering sequentially comprises first administering the pharmaceutical composition of the invention and a second administering comprising: (i) a glucocorticoid; or (ii) a glucocorticoid and the pharmaceutical composition of the invention.

In some embodiments, the co-administering sequentially comprises first administering: (i) a glucocorticoid; or (ii) a glucocorticoid and the pharmaceutical composition of the invention, and a second administering of the pharmaceutical composition of the invention.

In some embodiments, sequentially comprises at least 10 minutes apart, at least 20 minutes apart, at least 30 minutes apart, at least 45 minutes apart, at least 50 minutes apart, at least 1 hour apart, at least 2 hours apart, at least 3 hours apart, at least 5 hours apart, at least 8 hours apart, or at least 12 hours apart, or any value and range therebetween. Each possibility represents a separate embodiment of the invention.

In some embodiments, sequentially comprises 10-60 minutes apart, 20-90 minutes apart, 30-120 minutes apart, 1-3 hours apart, 2-6 hours apart, 3-9 hours apart, or 2-12 hours apart. Each possibility represents a separate embodiment of the invention.

In some embodiments, the at least one cannabinoid, the at least one terpene, or both, are present in the pharmaceutical composition in an amount of at least: 0.1 ng, 0.5 ng, 1 ng, 10 ng, 50 ng, 100 ng, 500 ng, 1 mg, 2 mg, 3 mg, 4 mg, 5 mg, 10 mg, 20 mg, 50 mg, 100 mg, 500 mg, or any value and range therebetween. Each possibility represents a separate embodiment of the invention. In some embodiments, the at least one cannabinoid, the at least one terpene, or both, are present in the pharmaceutical composition in an amount of ranging from: 0.1-100 ng, 1-1,000 ng, 100 ng-1,000 ng, 100 ng-10 mg, 1-100 mg, or 1-1,000 mg. Each possibility represents a separate embodiment of the invention.

In some embodiments, the subject is afflicted with or at increased risk of developing an inflammatory disease. In some embodiments, the subject is afflicted with or at increased risk of developing an IgE-related disease.

As used herein, the term "IgE-related disease" encompasses any disorder involving immunoglobulin E as part of the disorder pathogenesis, pathophysiology, or both. In some embodiments, IgE-related disease comprises any symptom or disorder associated therewith.

In some embodiments, the inflammatory disease comprises chronic rhinosinusitis.

In some embodiments, the inflammatory disease comprises chronic rhinosinusitis with nasal polyps.

In some embodiments, the subject is being treated with anti-chronic rhinosinusitis therapy or medication. In some embodiments, the subject is being treated with anti-chronic rhinosinusitis with nasal polyps.

In some embodiments, the subject is being treated with a steroid or any medication comprising same.

In some embodiments, the subject is being treated for chronic rhinosinusitis or chronic rhinosinusitis with nasal polyps with a steroid or any medication comprising same.

In some embodiments, the IgE-related disease comprises asthma. In some embodiments, the IgE-related disease comprises allergy.

In some embodiments, the subject is characterized by having increased serum levels of: Interleukin (IL)-4, IL-5, IL-13, high blood eosinophil cells' number and/or high blood eosinophil cells' number expressing eosinophil cationic protein (ECP), endocannabinoid/endocannabinoid-like/prostaglandin inflammatory profile, or any combination thereof.

In some embodiments, the subject is a mammal subject, such as, but not limited to a human.

In some embodiments, the subject is a human subject.

According to some embodiments, there is provided a method for preventing or treating a subject afflicted with a chronic rhinosinusitis with nasal polyps (CRSwNP), comprising administering to the subject a therapeutically effective amount of a pharmaceutical composition of the invention.

In some embodiments, the method comprises reducing the expression levels, serum levels, or both, of: IL-4, IL-5, IL-13, ECP, and blood eosinophil cells' number, or any combination thereof, of the subject.

In some embodiments, the method comprises reducing: cell proliferation, cell survival, cell functionally, or any combination thereof, of an immune cell, of the subject.

As used herein, the term "immune cell" refers to any cell of the host defense system within an organism which protects against disease, pathogens, other pathological agents or abnormalities, or divergence from homeostasis.

In some embodiments, the cell is a T lymphocyte. In some embodiments, the cell is an eosinophil. In some embodiments, the cell is an epithelial cell. In some embodiments, the cell is a macrophage cell. In some embodiments, the cell is a monocytic cell. In some embodiments, the cell is dendritic cell.

In some embodiments, cell functionality of an eosinophil comprises eosinophil cationic protein (ECP) expression, secretion, or both.

The term "expression" as used herein refers to the biosynthesis of a gene product, including the transcription and/or translation of the gene product. Thus, expression of a nucleic acid molecule may refer to transcription of the nucleic acid fragment (e.g., transcription resulting in mRNA or other functional RNA) and/or translation of RNA into a precursor or mature protein (polypeptide).

In some embodiments, "reducing" or "reduction" is at least: 2.5%, 3%, 4%, 5%, 10%, 15%, 20%, 30%, 40%, 50%, 60%, 70%, 80%, 90%, 95% or 100% reduction, or any value and range therebetween. Each possibility represents a separate embodiment of the invention. In some embodiments, "reducing" or "reduction" is 1-20%, 5-50%, 20-90%, 60-99%, 30-75%, 15-95%, or 85-100% reduction. Each possibility represents a separate embodiment of the invention.

In some embodiments, the method further comprises administering to the subject a therapeutically effective amount of a steroid. In some embodiments, the steroid comprises a low-dose steroid. In some embodiments, "low-dose steroid" is compared to a control or standard dose of steroid being administered to a subject treated solely with a steroid. In some embodiments, low-dose steroid is compared to a control or standard dose of steroid being administered to a subject not treated with the composition of the invention, not treated according to the herein disclosed method, or both.

In some embodiments, the herein disclosed composition enables to reduce the therapeutic effective amount of a steroid administered to a subject in need thereof, or completely save or spare a subject from steroid therapy.

In some embodiments, the subject is afflicted with asthma.

In some embodiments, the method further comprises a step of selecting a subject afflicted with asthma. In some embodiments, the method further comprises a step of determining a subject is afflicted with or has increased predisposition to developing asthma.

In some embodiments, a subject determined to be afflicted with asthma or having increased predisposition to developing asthma has increased suitability for treatment according to the herein disclosed method, compared to a control.

As used herein, the terms "treatment" or "treating" of a disease, disorder or condition encompasses alleviation of at least one symptom thereof, a reduction in the severity thereof, or inhibition of the progression thereof. Treatment need not mean that the disease, disorder or condition is totally cured. To be an effective treatment, a useful composition herein needs only to reduce the severity of a disease, disorder, or condition, reduce the severity of symptoms associated therewith, or provide improvement to a patient or subject's quality of life. In some embodiments, alleviated symptoms of the disease, disorder or condition include reduced cell viability, inhibited cell proliferation, reduced protein expression, secretion, or both. In some embodiments, reduced protein expression, secretion, or both, relates to IL-4, IL-5, IL-13, ECP, or any combination thereof.

Methods for determining protein expression, secretion, or both, are common and would be apparent to one of ordinary skill in the art. Non-limiting examples for methods of determining expression and/or secretion include, but are not limited to, RT-PCR, real time RT-PCR, next generation sequencing, western blot, dot blot, enzyme linked immunosorbent assay (ELISA), and other, some of which are exemplified hereinbelow (in the Example section).

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described compositions or composition prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, "treating" comprises ameliorating and/or preventing.

In some embodiments, "reduce" or "reducing" is compared to control, as disclosed herein.

In some embodiments, the subject is refractory to other nasal polyps' treatment/therapy.

In some embodiments, other nasal polyp's treatment/therapy comprises steroid treatment/therapy.

In one embodiment, refractory nasal polyps is steroid refractory nasal polyps—the steroid treatment does not treat, ameliorate or improve a clinical outcome or a clinical score in a subject afflicted with nasal polyps. In one embodiment, steroid refractory nasal polyps is characterized by deterioration in at least one nasal polyps' symptom, or a condition associated with nasal polyps.

Composition

According to some embodiments, there is provided a pharmaceutical composition comprising at least one cannabinoid for use in the reduction, prevention, or inhibition of growth of nasal polyps in a subject in need thereof.

In some embodiments, the subject is afflicted with or is at increased risk of developing an inflammatory disease.

According to some embodiments, there is provided a composition comprising: (a) at least one cannabinoid; (b) at least one terpene; or (c) a combination of (a) and (b), for use in the prevention or treatment of a chronic rhinosinusitis with nasal polyps (CRSwNP), in a subject in need thereof.

In some embodiments, the composition further comprises a pharmaceutically acceptable carrier.

In some embodiments, the composition is a pharmaceutical composition.

In one embodiment, the cannabinoid is not a psychoactive cannabinoid. In one embodiment, the composition does not comprise or is devoid of a psychoactive cannabinoid.

In some embodiments, the composition of the invention comprises at least 0.01%, 0.1%, 0.5%, 1%, 5%, 10%, 20%, 30%, 40%, 50%, 60%, 70%, 80%, 90%, 95%, 99% cannabinoids by weight of the composition, or any value and range therebetween. Each possibility represents a separate embodiment of the invention.

In some embodiments, the composition comprises or consists of a plant extract.

In some embodiments, the at least one cannabinoid is a synthetic cannabinoid.

As used herein, the term "extract" comprises the whole extract, a fraction thereof, a portion thereof, an isolated compound therefrom, or any combination thereof.

In some embodiments, the extract is derived from a plant material.

In some embodiments, the plant material is first dried and then extracted. In some embodiments, the plant material is air-dried. In some embodiments, the plant material is further heat treated (e.g., hot drying) and then extracted.

As used herein, the phrase "treatment before extraction" comprises, for example, sifting, freezing, drying, lyophilizing, or any combination thereof.

In some embodiments, the plant material is further processed prior to the extraction procedure in order to facilitate the extraction procedure. In some embodiments, processing methods prior to extraction, include but are not limited to sifting, crushing, slicing, or shredding, such as by using a grinder or other devices to fragment the plant parts into small pieces or powder.

In some embodiments, the extraction is a solvent-based extraction. In some embodiments, the solvent is a polar solvent. As used herein, a polar solvent may be selected from the group including, but not limited to, ethanol and Isopropyl alcohol. In some embodiments, the solvent is a non-polar solvent. In some embodiments, the extraction is a solvent-less-based extraction.

As used herein, the term "synthetic cannabinoid" refers to a compound that has a cannabinoid, endocannabinoid, cannabinoid-like, or endocannabinoid-like structure, and is manufactured using chemical means rather than by a plant or any other type of extraction apparent to one of ordinary skill in the art.

As used herein, the term "carrier", "excipient", or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier (e.g. carbomer, hydroxypropyl cellulose, sodium lauryl sulfate) as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S.¶ Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Colligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

A pharmaceutical composition may take any physical form necessary for proper administration. The composition comprising an encapsulated one or more cannabinoid compounds can be administered in any suitable form, including but not limited to a liquid form, a gel form, a semi-liquid (e.g., a liquid, such as a viscous liquid, containing some solid) form, a semi-solid (a solid containing some liquid) form, or a solid form. Compositions can be provided in, for example, a tablet form, a capsule form, a liquid form, a food form a chewable form, a non-chewable form, a transbuccal form, a sublingual form, a nasal form, a slow-release form, a non-slow-release form, a sustained release form, or a non-sustained-release form.

A pharmaceutically acceptable carrier suitable for the preparation of unit dosage form of a composition as described herein for peroral administration is well-known in the art.

In some embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), stabilizers (e.g. hydroxypropyl cellulose, hydroxypropylmethyl cellulose), viscosity increasing agents(e.g. carbomer, colloidal silicon dioxide, ethyl cellulose, guar gum lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), polymer coatings (e.g., poloxamers or poloxamines), and/or coating and film forming agents (e.g. ethyl cellulose, acrylates, polymethacrylates).

In some embodiments, preparation of effective amount or dose can be estimated initially from in vitro and/or ex-vivo assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures, tissue culture or experimental animals. In one embodiment, the data obtained from these in vitro and/or ex-vivo and/or cell culture assays and/or animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p.1].

In some embodiments, compositions for use in the methods of this invention comprise solutions or emulsions, which in some embodiments are aqueous solutions or emulsions comprising a safe and effective amount of the cannabinoids of the present invention and optionally, other compounds as described herein, including excipients intended for topical intranasal administration.

In another embodiment, the composition is administered by oral administration of a liquid preparation. In some embodiments, liquid formulations include solutions, suspensions, dispersions, emulsions, oils, aerosols, and the like. In another embodiment, the composition is administered nasally, and is thus formulated in a form suitable for nasal administration.

Further, in another embodiment, the composition is administered topically to body surfaces, and is thus formulated in a form suitable for topical administration. Suitable topical formulations include gels, ointments, creams, lotions, drops and the like. For topical administration, the active ingredients disclosed herein, e.g., one or more cannabinoids, are combined with an additional appropriate therapeutic agent or agents, prepared and applied as solutions, suspensions, or emulsions in a physiologically acceptable diluent with or without a pharmaceutical carrier.

In some embodiments, the composition is the form of a powder.

In some embodiments, the composition is dissolved in or comprises a lipophilic liquid and/or solvent. In some embodiments, the lipophilic liquid and/or solvent comprises or is oil.

In some embodiments, the oil is selected from: olive oil, sesame oil, medium chain triglyceride (MCT) oil, soy oil, sunflower oil, safflower oil, avocado oil, or any combination thereof.

In some embodiments, polar liquid or solvent is based on or comprises water (an aqueous solution or solvent).

In some embodiments, the composition is aseptic. In some embodiments, the composition is sterile or sterilized. In some embodiments, the composition is filtered.

In some embodiments, the composition is formulated as a spray or for spraying. In some embodiments, the composition is administered nasally as a spray, a nasal wash, nasal drops, or any combination thereof. In some embodiments, the method comprises nasally administering the composition being formulated as a spray or a nasal wash. In some embodiments, the administering comprises spraying the composition of the invention to the nasal cavity of a subject in need thereof. In some embodiments, the administering comprises washing the nasal cavity of a subject in need thereof with the composition of the invention.

In some embodiments, the composition of the invention further comprises at least one preserving agent.

Types of preserving agents, as well as their implementation into a pharmaceutical composition, are common and would be apparent to a person or ordinary skill in the art of pharmaceuticals.

In some embodiments, a composition for parenteral administration includes aqueous solution of the active preparation in water-soluble form. Additionally, suspensions of the active ingredients, in some embodiments, are prepared as appropriate oily or water-based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

Compositions are formulated, in some embodiments, for atomization and inhalation administration. In another embodiment, compositions are contained in a container with attached atomizing means.

In some embodiments, the composition is formulated for oral administration. In some embodiments, the composition is formulated for sublingual administration. In some embodiments, the composition is formulated for intranasal administration.

In some embodiments, administration comprises the use of a vaporizer. In some embodiments, administration comprises the use of a humidifier. In some embodiments, administration comprises the use of an inhaler or an inhalation device.

As used herein, a vaporizer, a humidifier, an inhalator, may receive a composition in a liquid form. In some embodiments, a vaporizer, a humidifier, an inhalator, may convert the composition into a vapor and/or an aerosol to be inhaled, or otherwise received by a subject.

The structure and operation of a vaporizer, a humidifier, an inhalator, will be apparent to one of ordinary skill in the art. However, in the interest of clarity, the elements of a vaporizer are briefly discussed. A vaporizer may include a cartridge, an atomizer, and a battery. The cartridge may include a reservoir to hold a liquid to be vaporized. The atomizer may include a heating element to convert the liquid into a vapor and/or aerosol. Optimally, the atomizer can vaporize the liquid without initiating combustion. The battery may have an electrical charge to power the atomizer and other accessories, for example, an indicator light that illuminates while the electronic cigarette is operating.

Vaporization provides many advantages over traditional combustion based methods of administering cannabinoids. For example, since a vaporizer can convert a composition into a vapor, the levels of each ingredient in the composition, including the cannabinoid, are controllable. Also, since vaporization does not involve combustion, a user may inhale or otherwise receive a bio-active ingredient, for example via inhalation, without being required to receive high levels of tar and various toxins associated with smoking. Vaporization also benefits from advantages such as rapid intake, direct delivery to the bloodstream, enhanced control of over- and under-dosage, and avoidance of respiratory disadvantages associated with combustion-based smoking. Vaporization may occur at approximately 180-190° C., which may significantly reduce pyrolytic smoke compound generation. Additionally, vaporization may occur below the typical point of combustion where smoke and associated toxins are generated (e.g., 230° C.).

In one embodiment, the amount of a composition to be administered will be dependent on the subject being treated, the severity of the affliction, the manner of administration, the judgment of the prescribing physician, etc.

The dosage administered will be dependent upon the age, health, and weight of the recipient, kind of concurrent treatment, if any, frequency of treatment, and the nature of the effect desired.

Kit

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

According to some embodiments, there is provided a kit comprising: (a) at least one cannabinoid selected from: CBD, CBG, THC, CBDV, and any combination thereof; and (b) at least one glucocorticoid.

In some embodiments, the kit, further comprises instructions for administering the at least one cannabinoid and the at least one glucocorticoid in a mole per mole (m/m) ratio ranging from 15:1 (m/m) to 1:1 (m/m), to a subject in need thereof.

According to some embodiments, there is provided a kit comprising: (a) at least one cannabinoid selected from the group consisting of: CBD, $\Delta^9$-THC, CBG, CBDV, CBC, and any combination thereof; and (b) at least one terpene selected from the group consisting of: Incensole acetate, Fenchol, Linalool, Humulene, Guaiol, Pinene, Carvacrol, Eucalyptol, 6-gingerol, Glycyrrhizin acid, Geraniol, Limonene, Lycopene, Terpineol, and any combination thereof.

In some embodiments, the kit further comprises instructions for administering the at least one cannabinoid CBD and the at least one terpene in a weight per weight (or molar) ratio ranging from 100:1 to 1:100, to a subject in need thereof.

In some embodiments of the subject kit, the at least one cannabinoid, the at least one terpene, or both, are packaged within a container.

In some embodiments, the container is made of a material selected from: thin-walled film or plastic (transparent or opaque), paperboard-based, foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments of the subject kit, the at least one cannabinoid and the at least one terpene are stored in separate containers within the main kit containment element e.g., box or analogous structure, may or may not be an airtight container, e.g., to further preserve the sterility of some or all of the components of the kit.

In some embodiments, the dosage amount of the at least one cannabinoid and the at least one terpene provided in a kit may be sufficient for a single application or for multiple applications.

In those embodiments, the kit may have multiple dosage amounts of the at least one cannabinoid and the at least one terpene packaged in a single container, e.g., a single tube, bottle, vial, Eppendorf, and the like.

In some embodiments, the kit may have multiple dosage amounts of the at least one cannabinoid and the at least one terpene antagonist individually packaged such that certain kits may have more than one container of the at least one cannabinoid and the at least one terpene.

In some embodiments, multiple dosage amounts of the at least one cannabinoid and the at least one terpene may be packed in single separate containers.

In some embodiments, the kit contains instructions for preparing the composition used therein and for how to practice the methods of the invention.

In some embodiments, the kit further comprises a measuring utensil such as syringe, measuring spoon or a measuring cup.

In some embodiments, the kit further comprises an inhalator.

In some embodiments, the kit further comprises a device configured to administer the composition of the at least one cannabinoid and the at least one terpene by inhalation.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "about" when combined with a value refers to plus and minus 10% of the reference value. For example, a length of about 1,000 nanometers (nm) refers to a length of 1,000 nm±100 nm.

It is noted that as used herein and in the appended claims, the singular forms "a", "an", and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological, and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods for Ex-Vivo Trial

Patients from three Medical Centers are evaluated by the principal investigator (PI) as part of their medical care at the Ear-nose and throat (ENT) clinic at the Tel Aviv Sourasky Medical Center, Assuta Tel Aviv Medical Center, and Shaare Zedek Medical Center. Nasal polyps (NP) steroid therapies are discontinued at least a week before surgery, while antihistamine treatments are discontinued at least three days before surgery. The removed NP are immediately immersed in phosphate saline buffer (PBS) and transported to Medi-Cane's R&D lab for ex-vivo analysis. In addition, 15 ml of peripheral blood (PB) is collected and transported to Medi-Cane for further analysis.

Informed consent is obtained before the surgery according to the Declaration of Helsinki. In addition, patients fill a basic health questionnaire.

The anti-inflammatory effect of cannabinoids and/or terpenes is evaluated in nasal polyp tissues, activated dispersed nasal polyp cells (DNPCs) and peripheral blood cells (PBCs) ex-vivo.

Dispersed Nasal Polyps Cells (DNPCs)

DNPCs are prepared from nasal polyps by means of enzymatic digestion. Nasal Polyps are incubated for 2 hours at 37° C. in RPMI 1640 (1 g of tissue per 4 mL) containing 2.0 mg/mL protease, 1.5 mg/mL collagenase, 0.75 mg/mL hyaluronidase, and 0.05 mg/mL DNase. The cell suspension is then filtered through a 70-mm cell strainer to remove any undigested tissue and washed 2 times with washing medium (RPMI 1640 supplemented with 2% FCS, 2 mmol/L glutamine, 100 U/mL penicillin, and 100 mg/mL streptomycin). The cell pellet is resuspended in erythrocyte lysis buffer and washed with washing medium. After washing, DNPCs are suspended in culture medium (RPMI 1640 supplemented with 10% Foetal Calf Serum (FCS), 2 mmol/L glutamine, 100 U/mL penicillin, and 100 mg/mL streptomycin).

Cell Cultures

In flat-bottomed, 48-well culture plates, 500 μL of 0.5×$10^6$/mL DNPCs are stimulated with recombinant *Staphylococcus Aureus* Enterotoxin B (SEB) (0.1-1 μg/mL), at 37° C. in a 5% $CO_2$/air condition for 72 h, with or without different concentrations and combination of isolated cannabinoids, terpenes and dexamethasone.

The effect of the treatment is evaluated by cell death parameters, using Propidium Iodate (PI) and flow cytometry (FACS) analysis, and enzymatic-linked immunoassay (ELISA).

NP Organ Culture

NP samples are cut in pieces (10-90 mg tissue weight each) and incubated in RPMI medium (0-10% FCS) with different concentrations and combinations of cannabinoids, terpenes, or dexamethasone for 3 h, 24 h and 72 h. Tissue weight is recorded at time zero, and again after incubation with vehicle or treatments. In addition, cell death is quantified by PI and flow cytometry following tissue enzymatic digestion.

In vitro Assay

Human T cells line (Jurkat) is cultivated with RPMI medium and treated with different concentrations and combinations of cannabinoids for 2 h. T cell death is quantified by PI and flow cytometry analysis.

Cytokine Determination

Cell cytokine production of typical Type II interleukins (IL-4, IL-5 and IL-13) is determined in culture supernatant by ELISA.

Cell Viability

Cell viability is assessed by FACS analysis of Propidium Iodate (PI), which is a membrane impermeant dye that is generally excluded from viable cells. After incubation time, DNPCs are stained with PI for 15 min and immediately analyzed using a FACS instrument.

Cell Proliferation

Proliferation of eosinophils and T cells is determined by labeling using the membrane proliferation marker carboxyfluorescein succinimidyl ester (CFSE).

Eosinophils Function

Eosinophil functionality is determined based on the secretion profile of the eosinophil cationic protein (ECP). ECP levels are assessed in IL-33 activated-DNPCs supernatant by ELISA test, according to manufacture instructions.

Peripheral Blood (PB) Analysis

Peripheral blood mononuclear cells (PBMCs) are collected for the analysis of the effect of the different cannabinoids and/or terpenes combinations in vitro. Briefly, 5 milliliters of patients' PB are collected in EDTA tubes just before NP removal and PBMCs are isolated using density gradient. After washing the PBMCs in PBS, cells are suspended in culture medium and cannabinoids, terpenes, and their combinations, are tested at concentrations ranging from 0.1 nM to 1.5 mM. Cell viability, proliferation, and cytokine production are examined as described above.

Peripheral blood serum is collected for analysis of endocannabinoids, endocannabinoid-like molecules, prostaglandins, and cytokines.

The control, dexamethasone, is applied (alone or together with cannabinoids, terpenes, or their combination) in the following concentrations: 0.1, 1, 5, 10, and 150 μM, and 300 μM.

Water soluble dexamethasone is used (SIGMA-D2915-Lot #SLCC3493).

Stock solutions of 20 mg/ml, 10 mg/ml, and 1 mg/ml are prepared in PBS.

Dilutions are prepared Dulbecco's Phosphate Buffered Saline minus $Ca^{2+}$ minus $Mg^{2+}$(Biological Industries, Beit Haemek, Israel-Catalog No 02-023-1A-Lot #2104085).

Patients

Thirty to fifty (30-50) patients enrolled in three clinical sites including: the Tel Aviv Sourasky Medical Center, Assuta Tel Aviv Medical Center, and Shaare Zedek Medical Center.

Age—20-70 years old.

Sex—men and women.

Inclusion Criteria

Patients aged 20-70 years old with a diagnosis of nasal polyps.

Patients can present concomitant diagnosis of asthma for a period of at least 6 months prior to screening.

Patients who present asthma disease should be on stable asthma treatment of at least inhaled corticosteroids with or without any other required, inhaled asthma medication.

Peripheral blood eosinophils level ≥300 cells/μL.

Exclusion Criteria

Unable to provide informed consent.

Patients with a concurrent diagnosis of a corticosteroid-dependent condition, cystic fibrosis, granulomatous sinonasal disorder (granulomatosis with polyangiitis, sarcoidosis).

Patient with immunosuppressive diagnosis (human immunodeficiency virus, hematologic malignancy or transplant history).

Asthma exacerbation, within 6 weeks prior to screening, which required systemic corticosteroids, hospitalization or emergency room visit.

Use of biological medication for asthma, NP or CR or any other indications that has the potential to interfere/affect either asthma or nasal polyposis disease progression, within 6 months of screening.

Use of medication for sinonasal symptoms (antibiotics with or without OCS) within 30 days of screening or during the run-in period.

Use of tetracycline or macrolide antibiotics specifically, within 8 weeks of screening.

Pregnant and nursing women.

Example 1

CBD Induces Detachment of Human Nasal Polyp Cells/Tissues Ex-Vivo

The inventors showed that following a 3 h incubation of human nasal polyp (NP) whole tissues with CBD (150 μM), cells/tissue pieces were starting to detach from the main NP whole tissue (FIG. 1).

Figure 2:
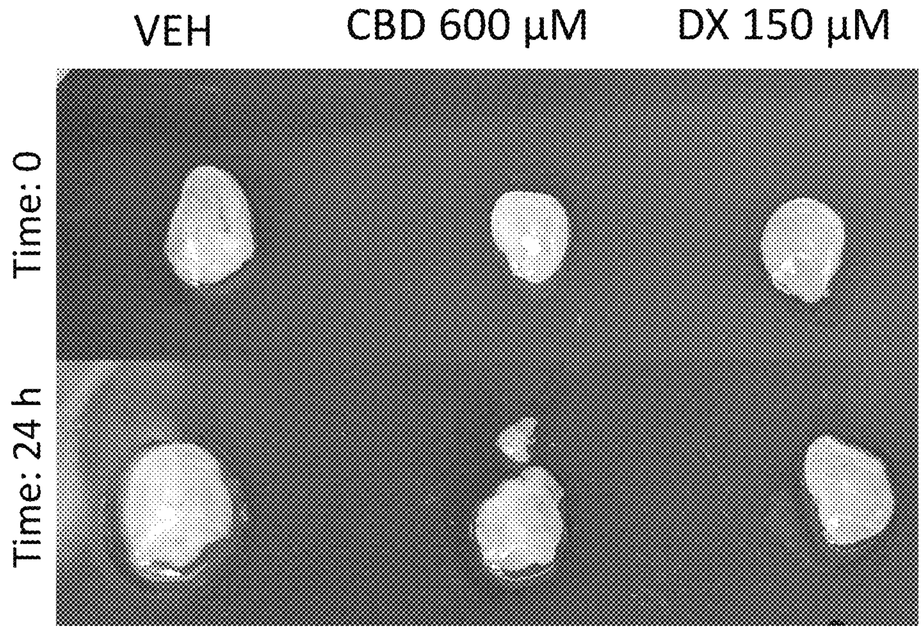
FIG. 2 includes a micrograph showing the effect of 24 h of incubation of nasal polyps with CBD, dexamethasone (DX), or vehicle (VEH). CBD and DX were applied at a concentration of 600 μM and 150 μM, respectively. In nasal polyps treated with CBD, a significant detachment of nasal polyp cells/pieces, was observed.

Further, the inventors showed that after a 24 h incubation of human NP tissues with CBD (600 μM), DX (150 μM), or vehicle—CBD (600 μM) caused significant detachment of cells/tissues from the main NP whole tissue (FIG. 2).

Figure 3:
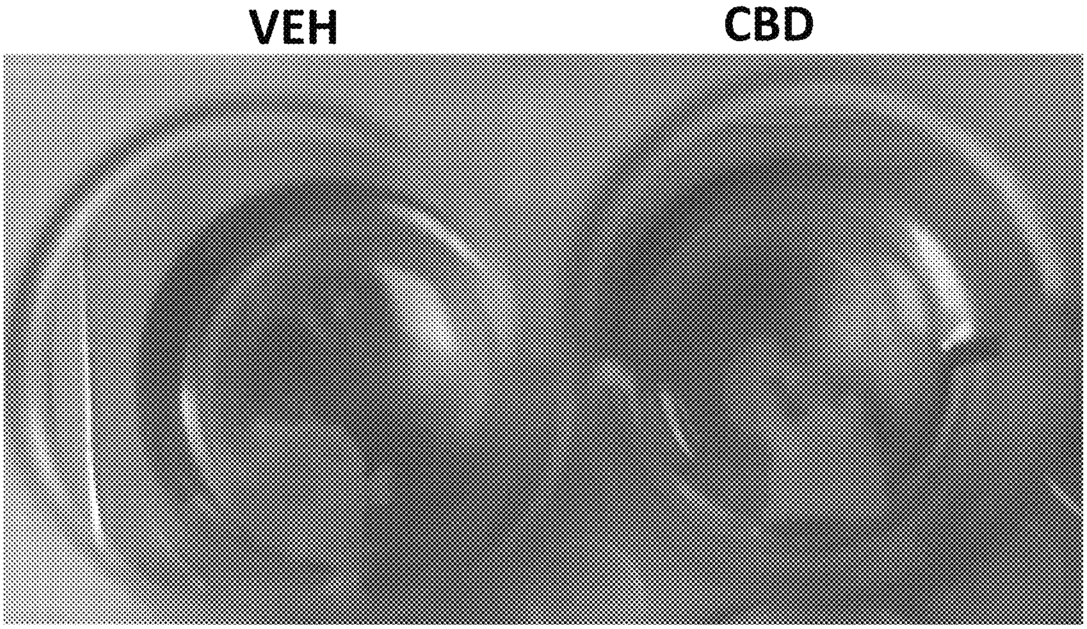
FIG. 3 includes a micrograph showing that 72 h post incubation of nasal polyps with CBD (150 μM), cells/tissue pieces are breaking off the main polyp into the medium. Vehicle-VEH.

After 72 h incubation of human NP whole tissues with CBD (150 μM), the inventors documented cells/tissue pieces breaking off the main polyp into the medium (FIG. 3).

Example 2

Figure 4:
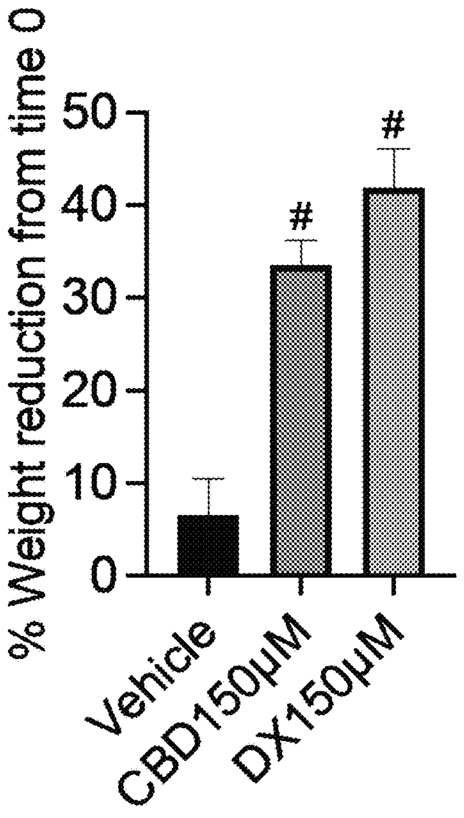
FIG. 4 includes a vertical bar graph showing that CBD induces a significant nasal polyp weight reduction (similar to the effect of DX) after 3 h of incubation. CBD and DX were applied at a concentration of 150 μM. (Significant One-Way ANOVA with LSD post hoc, #, p<0.002).

The Effect of Cannabinoids, Glucocorticoid, or their Combination on Human NP Tissue Weight Ex-Vivo The inventors showed that following a 3 h incubation of human NP with CBD (150 μM) ex-vivo, a significant tissue weight reduction was observed (FIG. 4). This effect is similar in magnitude to the effect of standard of care (SOC), that is—dexamethasone (DX; 150 μM).

Figure 5:
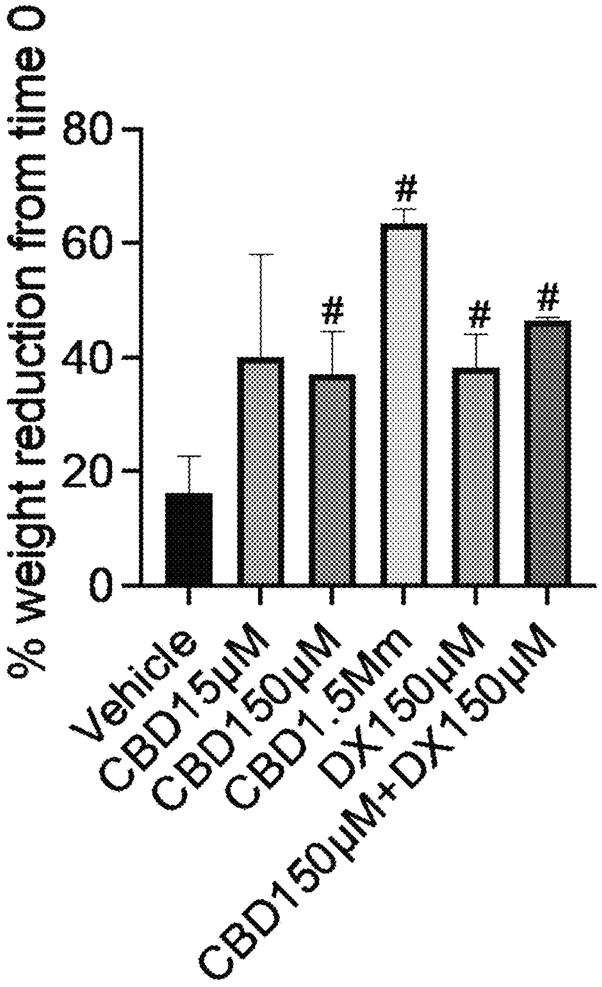
FIG. 5 includes a vertical bar graph showing that CBD induces significant dose-dependent nasal polyp weight reduction after 24 h of incubation. CBD was applied at concentrations of: 15 μM, 150 μM, and 1.5 mM. DX was applied at a concentration of 150 μM, either alone or with 150 μM of CBD.

Further, the inventors showed that after 24 h of incubation, CBD induced significant human NP tissue weight reduction ex-vivo, in a dose-dependent manner (150 μM to 1.5 mM; FIG. 5). The effect of DX at 150 μM was comparable to CBD 150 μM. No additive or synergistic effect was observed when CBD and DX were co-administered at a molar ratio of 1:1. The inventors showed a similar trend of NP weight reduction for CBG (at 150 μM; 13A-13B).

Figure 6:
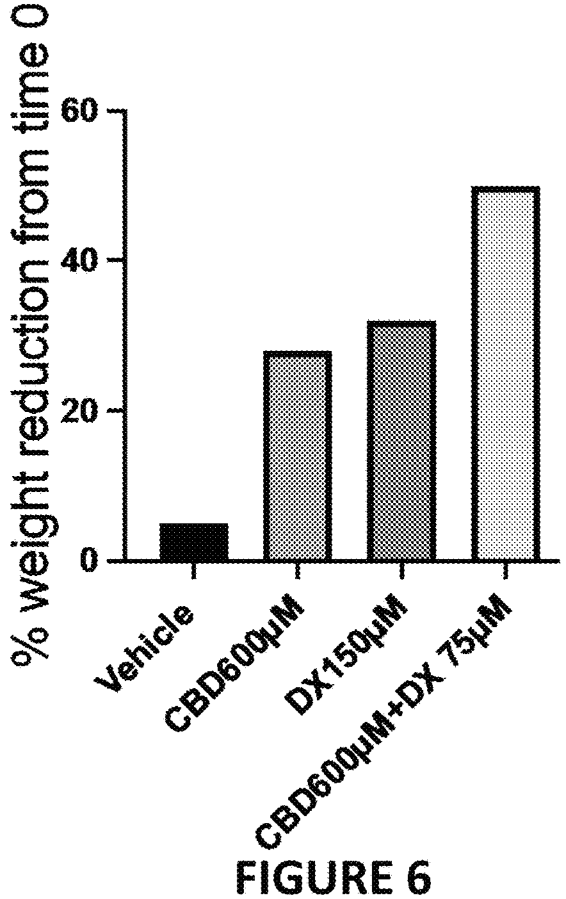
FIG. 6 includes a vertical graph showing that a mixture of CBD and reduced DX dose results in an additive effect on weight reduction of incubated nasal polyps. A similar effect on nasal polyp weight reduction was observed for CBD applied alone at a concentration of 600 μM and for DX applied at a concentration of 150 μM. Combining CBD (600 μM) with a low dose of DX (75 μM) resulted in an increased effect of nasal polyp weight reduction.

Further, the inventors examined whether an additive effect could be achieved for different molar ratios of CBD to DX. Specifically, the inventors have shown that a high dose CBD (600 μM) co-administered with a low dose DX (75 μM) provides an additive inhibitory effect on human NP tissue growth or size, ex-vivo (FIG. 6).

Therefore, the inventors conclude that a combination of a high-dose cannabinoid, e.g., CBD, with low-dose DX, either provided concomitantly, or sequentially, can provide the desired additive inhibitory effect on human NP tissue growth or size. To this end, the cannabinoid may be administered first, thus providing a fast-acting activity, which is further complemented by a later administration of DX, hence achieving the desired additive inhibitory effect on human NP tissue growth or size.

Example 3

Figure 7:
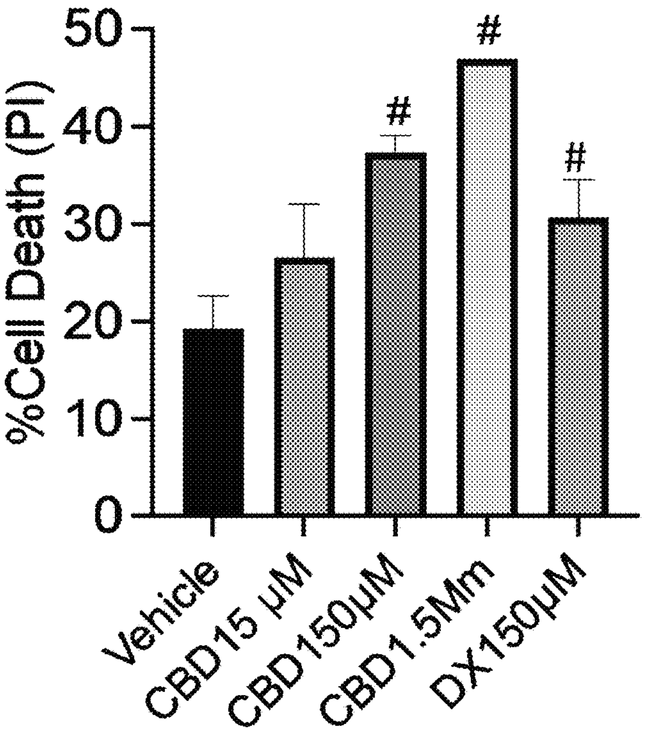
FIG. 7 includes a vertical bar graph showing that CBD significantly increased the percent of dead cells in enzymatically dissociated nasal polyps 24 h post incubation, in a dose-dependent manner. Human nasal polyp tissues were removed during surgery, placed in a growth medium, and incubated with: Vehicle, CBD, or DX. Twenty-four hours (24 h) post incubation a significant increase in cell death was observed in the presence of CBD (quantified by propidium iodide (PI)-positive staining in flow cytometry). CBD was applied at concentrations of: 15 μM, 150 μM, and 1.5 mM. DX was applied at a concentration of 150 μM. (Significant One-Way ANOVA with LSD post hoc, #, p<0.03).

Cannabinoids, Glucocorticoid, or their Combination Induces Cell Death of Dissociated Human NP Cells The inventors showed that CBD treatment significantly increased the percent of dead cells in enzymatically-dissociated human NP (FIG. 7).

Figure 9:
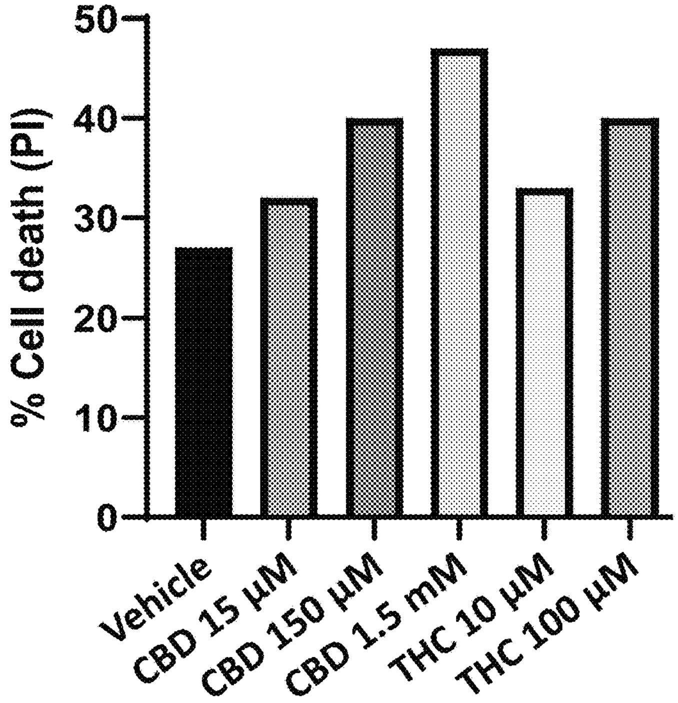
FIG. 9 includes a vertical bar graph showing the effect of tetrahydrocannabinol (THC) on the viability of nasal polyp cells. THC at concentrations of 10 μM and 100 μM had comparable effect as CBD at 15 μM and 150 μM, respectively, after 24 hours of incubation.

Further in the context of % cell death, the inventors showed that a treatment with 100 μM of THC provided a comparable effect to CBD at a concentration of 150 μM (FIG. 9).

Figure 10:
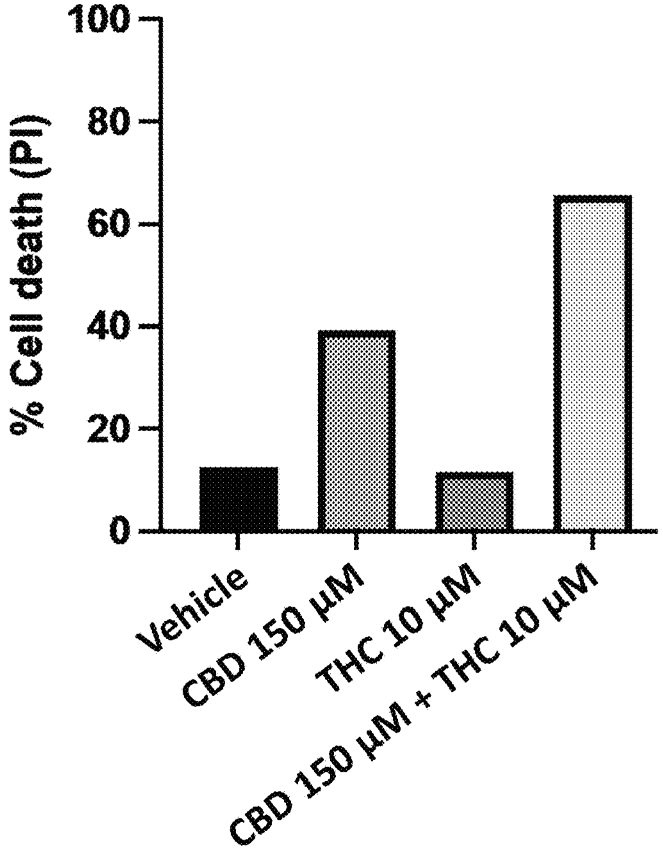
FIG. 10 includes a vertical graph showing that a mixture of CBD together with a reduced THC dose results in an additive effect on increased cell death in incubated nasal polyps, after 72 hours of incubation. CBD applied alone at a concentration of 150 μM induced substantial cell death of incubated nasal polyp cells. The effect of THC at a concentration of 10 μM was negligible (comparable to vehicle). However, CBD (150 μM) and low dose THC (10 μM) had superior effect, resulting in an increased % of cell death (approx. 70%).

Further, the inventors examined whether a synergistic or an additive effect could be achieved for a combination of CBD and THC. Specifically, the inventors have shown that CBD (150 μM) co-administered with a low dose THC (10 μM) provides a better than an additive effect or a synergistic effect of promoting cell death (FIG. 10).

Further, the inventors showed that CBG (at 150 μM) has induced a substantial cell death of NP cells (13C-13D).

Therefore, the inventors conclude that a combination of a first cannabinoid, e.g., CBD, with a second cannabinoid at a low-dose, e.g., THC, can provide the desired synergistic effect of promoting cell death, thus inhibiting or reducing human NP tissue growth or size. To this end, the cannabinoids may be administered concomitantly or sequentially.

Example 4

Figure 12:
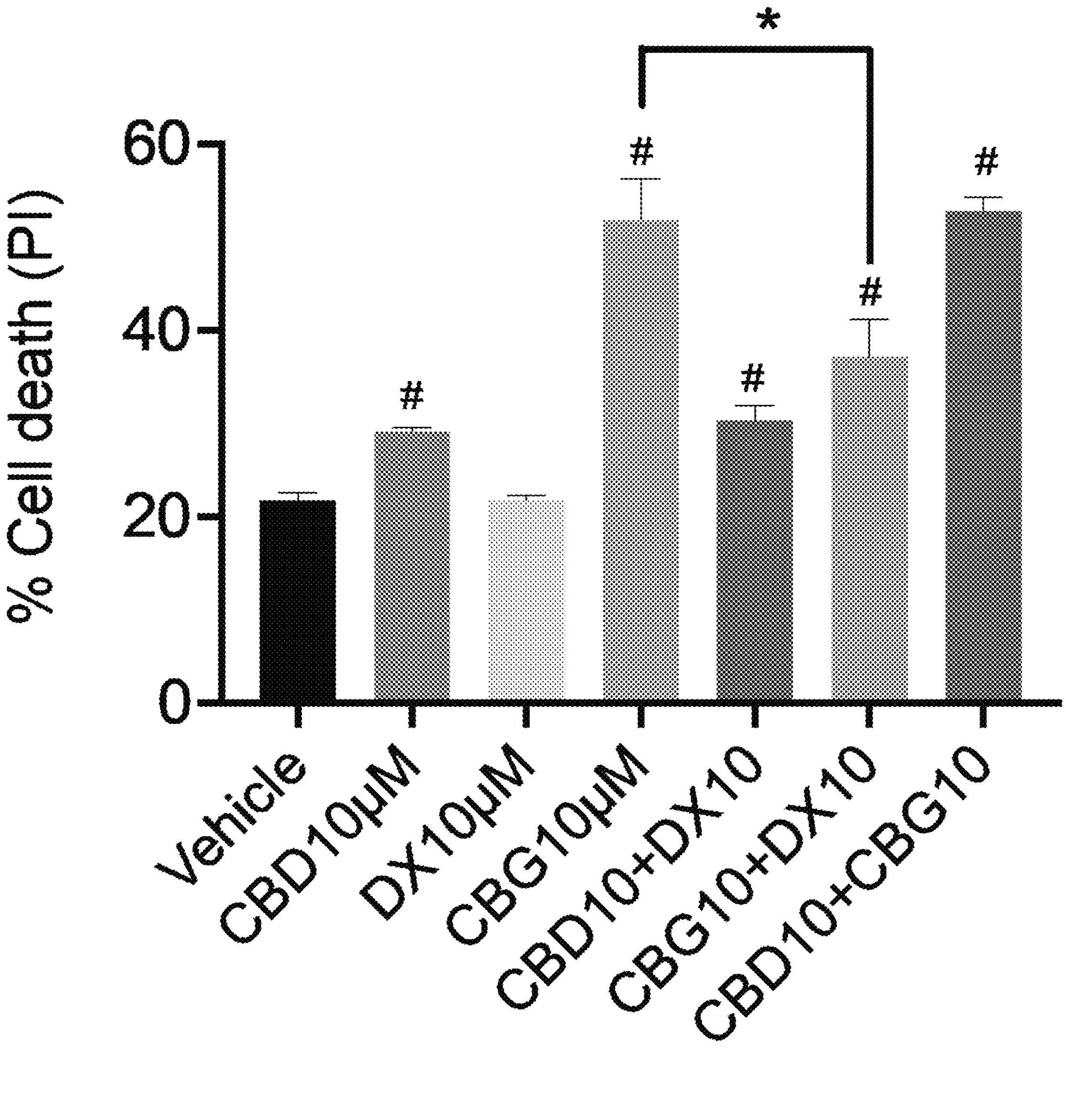
FIG. 12 includes a vertical bar graph showing the effects of CBD, CBG, DX, at 10 μM doses, or combinations thereof, on cell death of dispersed nasal polyp cells. Cell were incubated with cannabinoids or DX for 2 h to evaluate the fast-acting effect of the different cannabinoids, or their combinations on nasal polyp cell death. The cannabinoids CBD and CBG showed a significant increase in cell death after 2 h of incubation. This effect was not observed for DX. (Significant One-Way ANOVA with LSD post hoc, #, p<0.01, *<0.001).
Figure 13A:
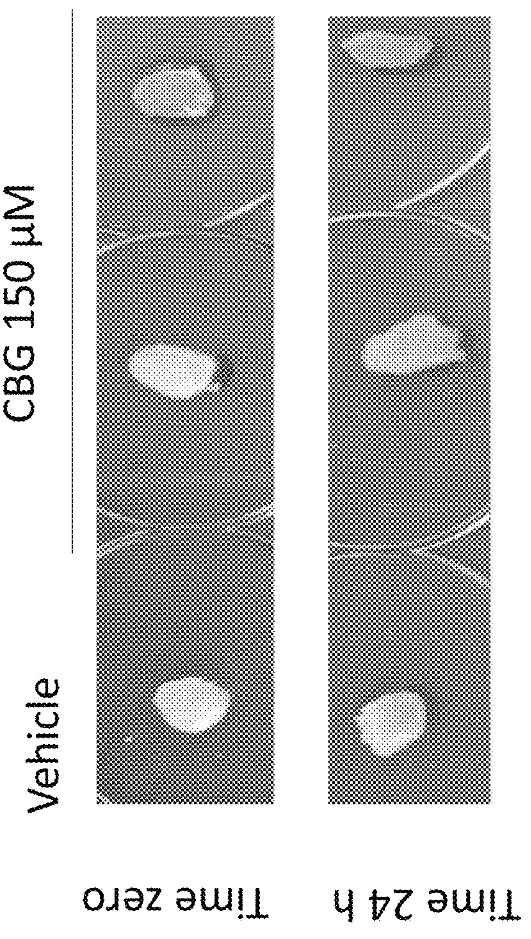
FIGS. 13A-13D include micrographs and graph showing the effect of CBG on nasal polyp cells/tissue pieces size and cell survival. (13A) A micrograph showing that after 24 h of CBG (150 μM) incubation, the size of nasal polyps is reduced. (13B) A vertical bar graph showing % weight reduction (13A). (13C) A micrograph showing the effect of CBG on the viability of nasal polyp cells. CBG at a concentration of 150 μM had induced substantial cell death of incubated nasal polyp cells. (13D) A vertical bar graph showing % cell of NP of (13C).
Figure 13B:
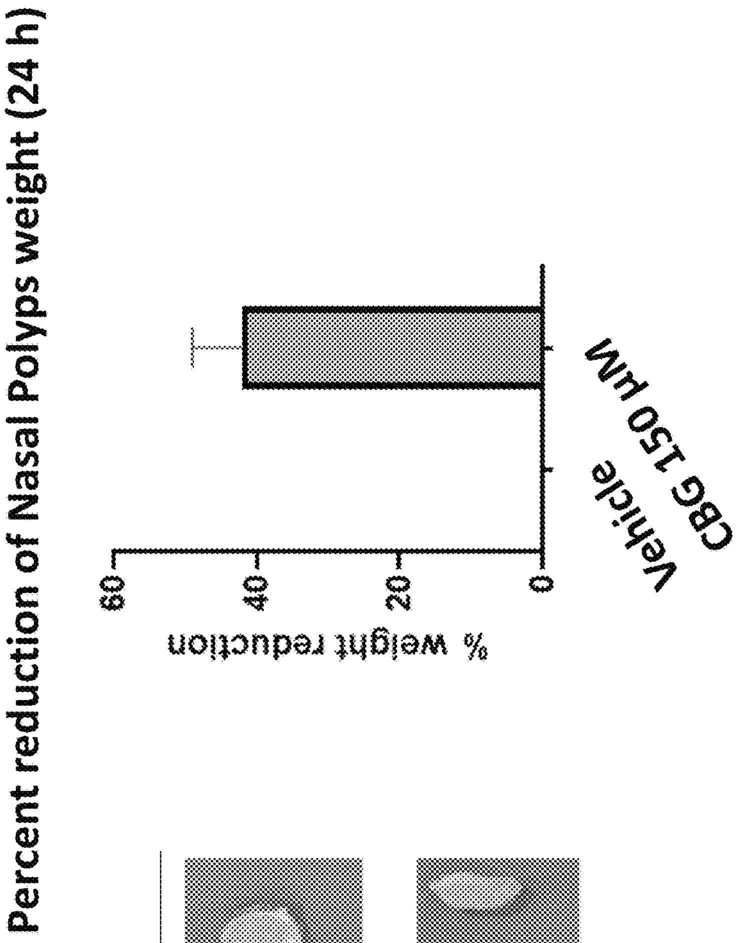
Figure 13D:
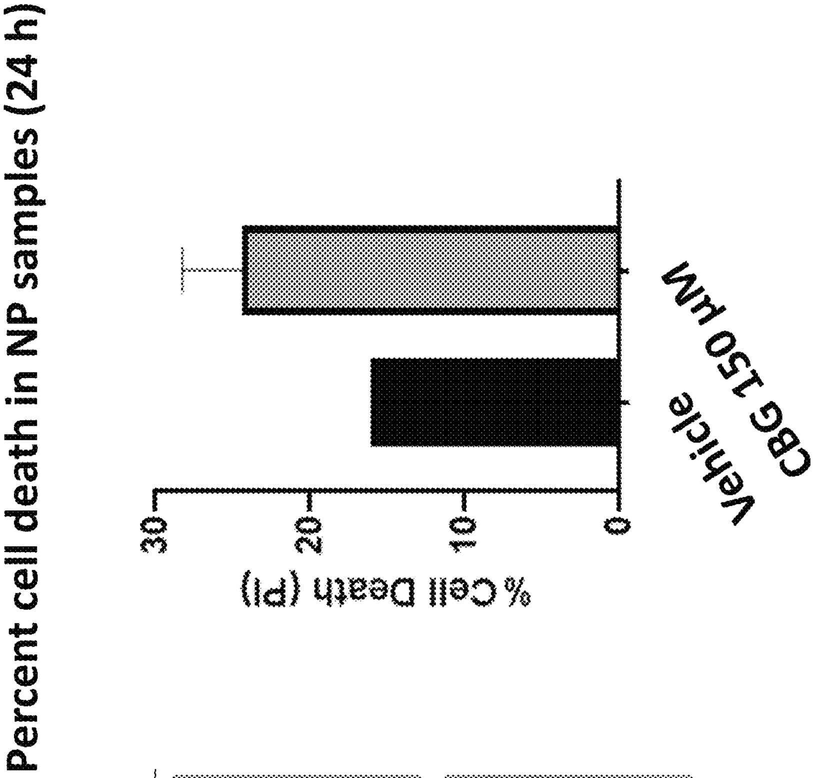
Figure 13C:
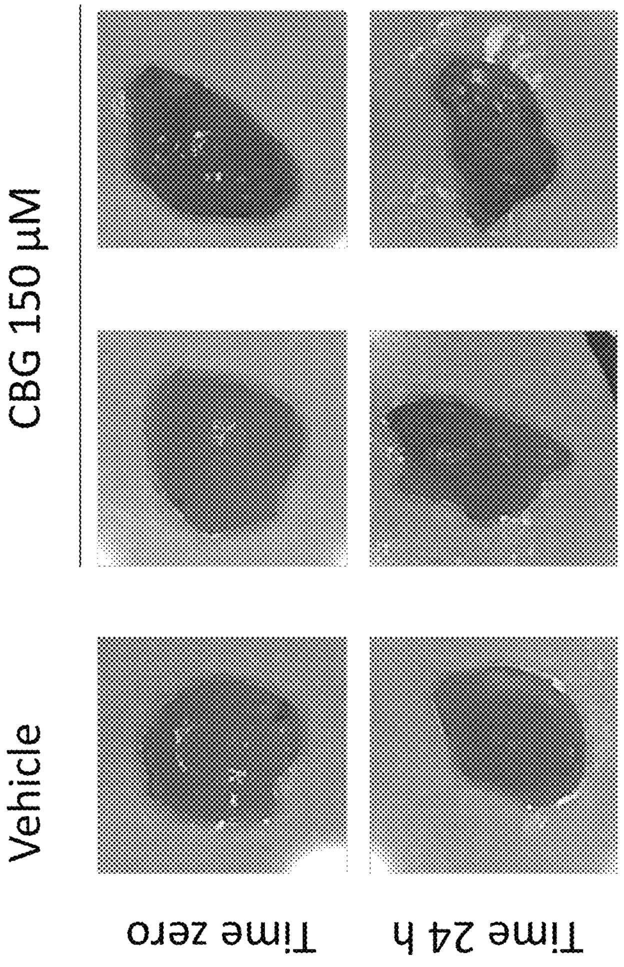

The Effect of Cannabinoids, Glucocorticoid, or their Combination on Dispersed NP Cells The inventors have examined the effects of CBD, CBG, DX, or combinations thereof at a concentration of 10 μM, on cell death of dispersed NP cells. Cell were incubated with: (i) CBD; (ii) CBG; (iii) DX; (iv) CBD+DX; (v) CBG+DX; and (vi) CBD+CBG, for 2 h to evaluate the fast acting effect of the compounds (e.g., cannabinoid, and glucocorticoid) or their combinations on NP cell death. The cannabinoids CBD and CBG induced a significant increase in cell death % after 2 h of incubation (FIG. 12). This is in sharp contrast with the activity of DX, which was similar to the activity observed in the vehicle group (negative control) after this time period.

Further, the inventors showed that the combination of CBG+DX (at a 1:1 molar ratio; 10 μM of each) showed a significant reduction in NP cell death promoting activity, as compared to CBG alone (10 μM; FIG. 12). Thus, the inventors conclude that it may be preferable to administer CBG and DX so as to inhibit or reduce NP size or growth, wherein CBG and DX are provided sequentially apart from one another, such that CBG is initially provided, and DX is provided to the subject only at a later time.

Example 5

The Effect of Cannabinoids on the Survival of Lymphocytes

Figure 11:
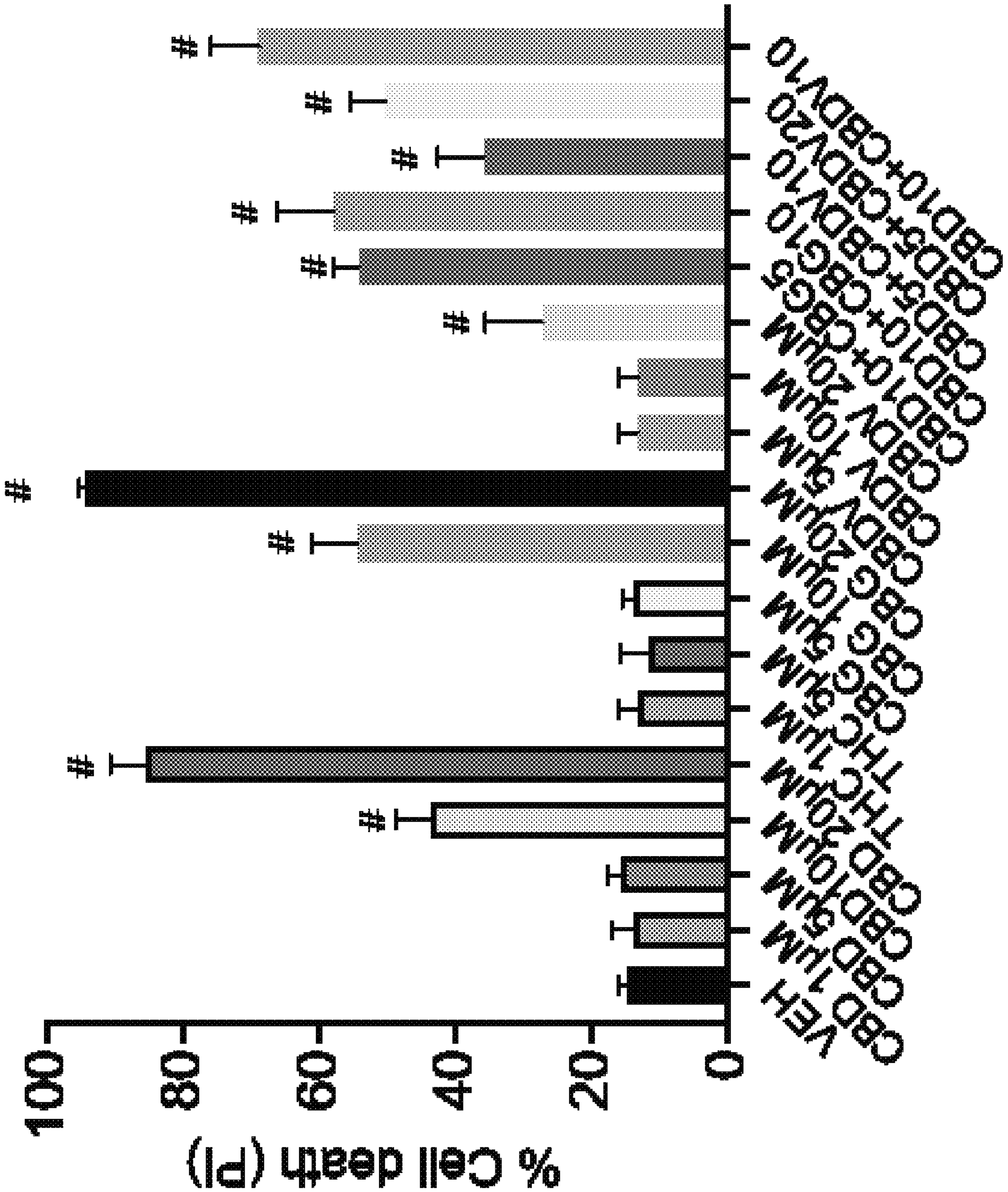
FIG. 11 includes a vertical bar graph showing the effect of various cannabinoids, or their combination, on T cell survival. The effect on cell death in human Jurkat T cell line was examined in the presence of CBD (1 μM, 5 μM, 10 μM, and 20 μM), THC (1 μM, and 5 μM), cannabigerol (CBG; 5 μM, 10 μM, and 20 μM), cannabidivarin (CBDV; 5 μM, 10 μM, and 20 μM), and the following combinations: CBD 10 μM+CBG 5 μM; CBD 10 μM+CBG 10 μM; CBD 5 μM+CBDV 10 μM; CBD 5 μM+CBDV 20 μM; and CBD 10 μM+CBDV 10 μM. (Significant One-Way ANOVA with LSD post hoc, #,p<0.04).

The inventors have further examined the effect of various cannabinoids on the survival of T cells, which are known to be involved in chronic rhinosinusitis with nasal polyposis. The inventors showed that both CBD and CBG had induced a significant cell death compared to control (vehicle; FIG. 11). Further, CBDV was also shown to induce cell death, when provided at a concentration of 20 μM.

Example 6

The Effect of CBD on Dispersed NP Cells in a Bacterial Infection Model

Figure 8:
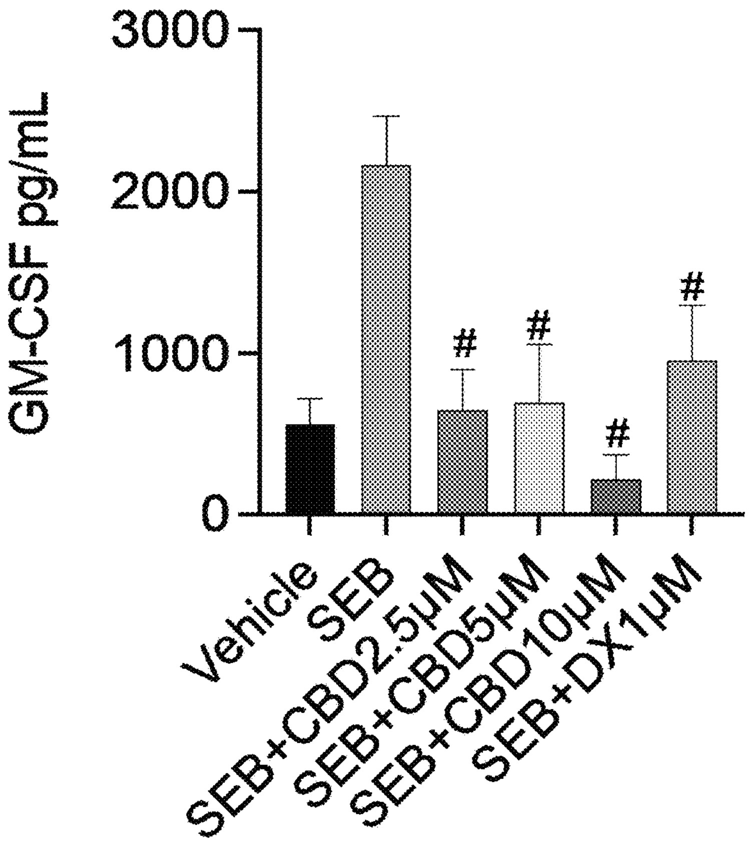
FIG. 8 includes a vertical bar graph showing that CBD significantly reduces or inhibits level of granulocyte-macrophage colony-stimulating factor (GM-CSF). Staphylococcal Enterotoxin type B (SEB), used herein as a model of bacterial infection in nasal polyposis, induces increase in GM-CSF levels in dispersed nasal polyp cells. CBD was applied at concentrations of: 2.5 μM, 5 μM, and 10 μM, 30 min before SEB. DX was applied at a concentration of 1 μM 30 minutes before SEB. (Significant One-Way ANOVA with LSD post hoc #, p<0.01).

SEB increases Granulocyte-macrophage colony-stimulating factor (GM-CSF) in dispersed nasal polyp cells. GM-CSF is known to stimulate stem cells to produce granulocytes. CBD, (like DX) was shown to significantly decrease this glycoprotein at different doses (FIG. 8), thus inhibiting granulocyte proliferation. This may reduce the number of accumulating cells in the NP during infection.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for inhibiting the growth of a nasal polyp or reducing: the volume, the mass, the number of cells, or any combination thereof in a nasal polyp in a subject in need thereof, comprising administering to said subject a therapeutically effective amount of a pharmaceutical composition comprising CBD and THC in a mole per mole ratio (m:m) of about 15:1, and a pharmaceutically acceptable carrier, thereby inhibiting the growth of the nasal polyp or reducing: the volume, the mass, the number of cells, or any combination thereof in a nasal polyp in the subject.

2. The method of claim 1, further comprising a step of co-administering to said subject a therapeutically effective amount of a glucocorticoid.

3. The method of claim 2, wherein said glucocorticoid is dexamethasone or functional analog thereof.

4. The method of claim 2, wherein said glucocorticoid and said pharmaceutical compositions are co-administered sequentially or concomitantly.

5. The method of claim 1, wherein said subject is afflicted with chronic rhinosinusitis.

6. The method of claim 5, wherein said chronic rhinosinusitis comprises chronic rhinosinusitis with nasal polyps.

7. The method of claim 1, wherein said administering is orally administering, nasally administering, or both.

8. The method of claim 1, wherein said administering is contacting said nasal polyp with said pharmaceutical composition.

* * * * *